United States Patent [19]

Mehl

[11] Patent Number: 4,469,109

[45] Date of Patent: Sep. 4, 1984

[54] BONE MARROW ASPIRATION NEEDLE

[75] Inventor: Donald N. Mehl, Minnetonka, Minn.

[73] Assignee: Creative Research and Manufacturing Inc., Minnetonka, Minn.

[21] Appl. No.: 334,427

[22] Filed: Dec. 24, 1981

[51] Int. Cl.³ .............................................. A61B 10/00
[52] U.S. Cl. .................................... 128/753; 128/754; 128/310
[58] Field of Search .............................. 128/751–755, 128/310, 347, 221, 61 C; 145/61 C; 403/348, 349; 604/272

[56] References Cited

U.S. PATENT DOCUMENTS

| | | | |
|---|---|---|---|
| 1,696,462 | 12/1928 | Victor | 403/349 |
| 1,932,099 | 10/1933 | Cabana | 403/349 |
| 3,470,604 | 10/1969 | Zenick | 128/221 |
| 3,585,986 | 10/1971 | Krug | 128/221 |
| 3,628,524 | 12/1971 | Jamshidi | 128/347 |
| 3,893,445 | 7/1975 | Hofsess | 128/754 |
| 3,955,451 | 5/1976 | Lohness | 145/61 C |
| 4,010,737 | 3/1977 | Vilaghy et al. | 30/316 |
| 4,249,541 | 2/1981 | Pratt | 128/753 |
| 4,256,119 | 3/1981 | Gauthier | 128/754 |
| 4,258,722 | 3/1981 | Sessions et al. | 128/753 |
| 4,262,676 | 4/1981 | Jamshidi | 128/310 |
| 4,266,555 | 5/1981 | Jamshidi | 128/754 |
| 4,314,565 | 2/1982 | Lee | 128/754 |

FOREIGN PATENT DOCUMENTS 434028 1/1912 France .......................... 604/272

Primary Examiner—Richard J. Apley
Assistant Examiner—Harry Macey
Attorney, Agent, or Firm—Hugh D. Jaeger

[57] ABSTRACT

Needle for bone marrow biopsies including a cannula, a cannula housing supporting the cannula including a partially threaded lower member, a stylet including a stylet cap supporting the stylet and a threaded depth stop for engaging over the cannula wherein the stylet engages into the cannula in a predetermined relationship, the stylet cap interlocks to the cannula housing, and the threaded member determines the depth of penetration of the needle. The sternum needle is constructed to be either disposable or reusable depending upon the cannula housing and stylet cap material. The cannula housing includes vertical wings extending outwardly from the housing for engagement with the palm of a physician's hand, a cannula clip having ends which are soldered onto the cannula and secure into the cannula housing, and an elongated button extending outwardly from the top of the cannula housing for detent locking with the stylet cap providing for alignment of the stylet to the cannula of the sternum needle. The stylet includes a longitudinal member having a ground and buffed beveled end maintaining a knife-sharp edge around the tip, and the other end of the stylet is bent and molded into the stylet cap where the stylet cap includes a spring detent locking groove for interlocking with the button of the cannula housing. The stylet cap is rounded at the top and includes vertical grooves for gripping during locking and unlocking.

5 Claims, 7 Drawing Figures

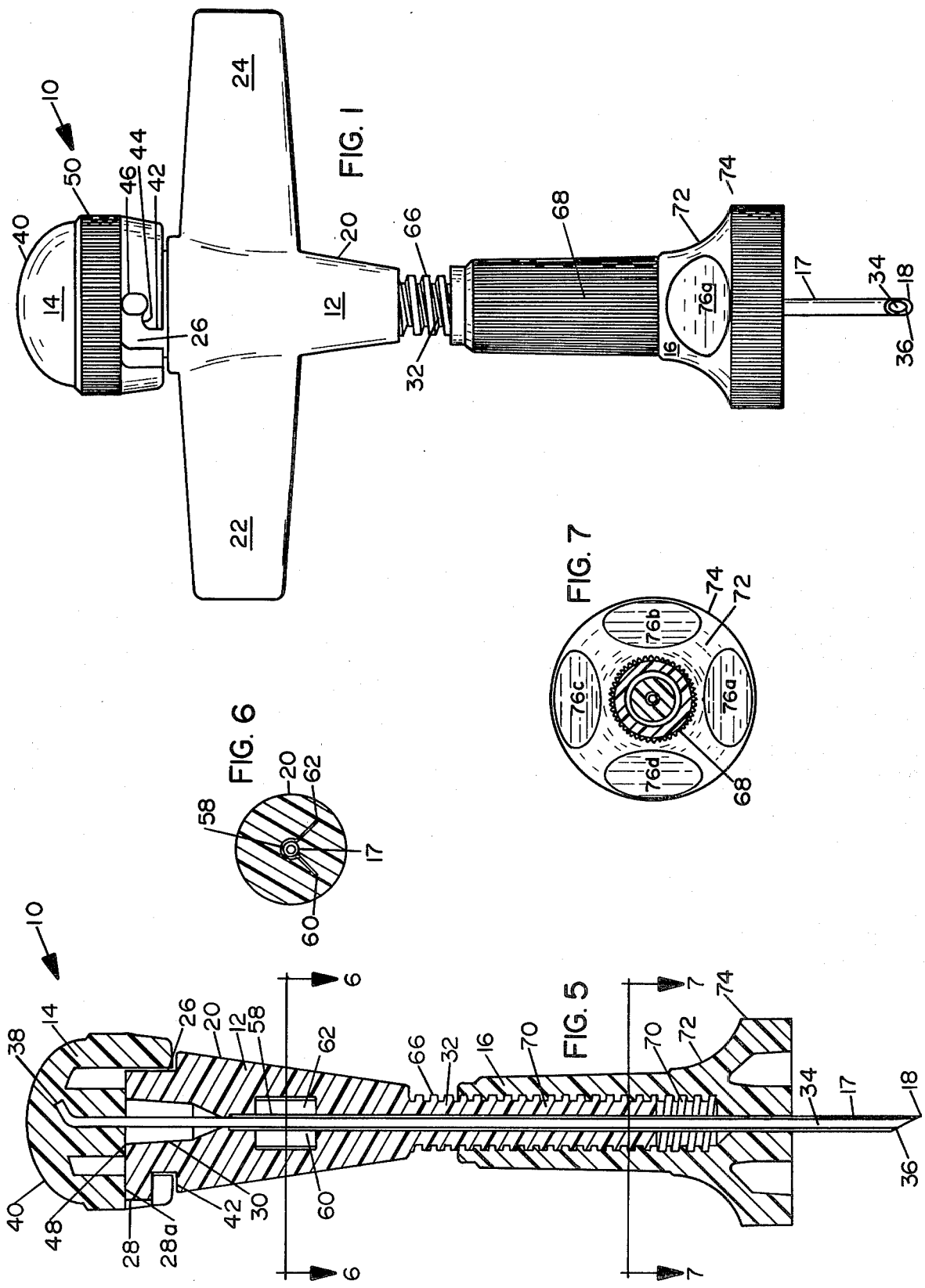

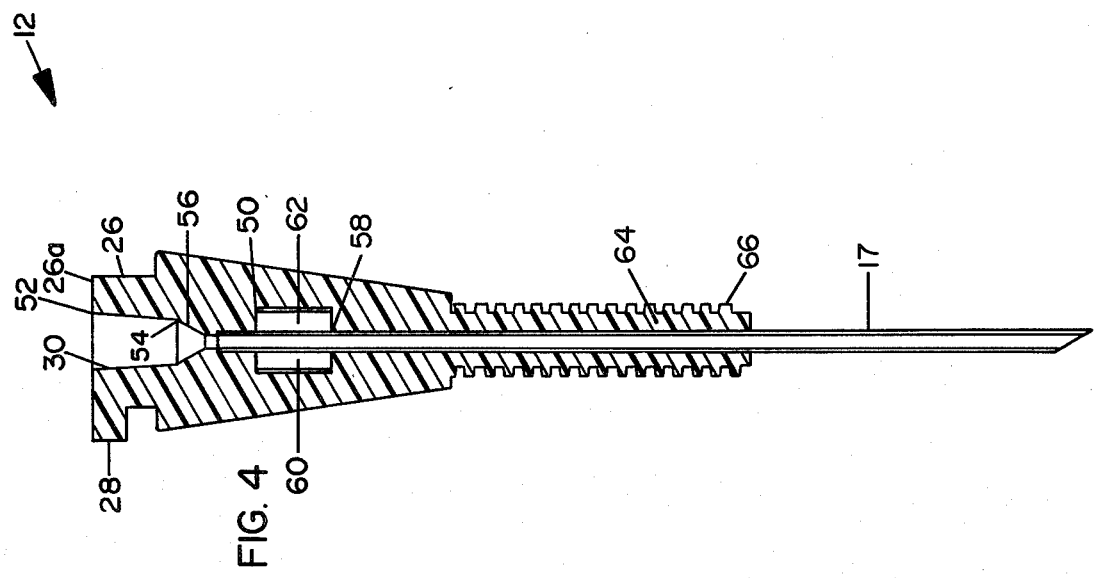
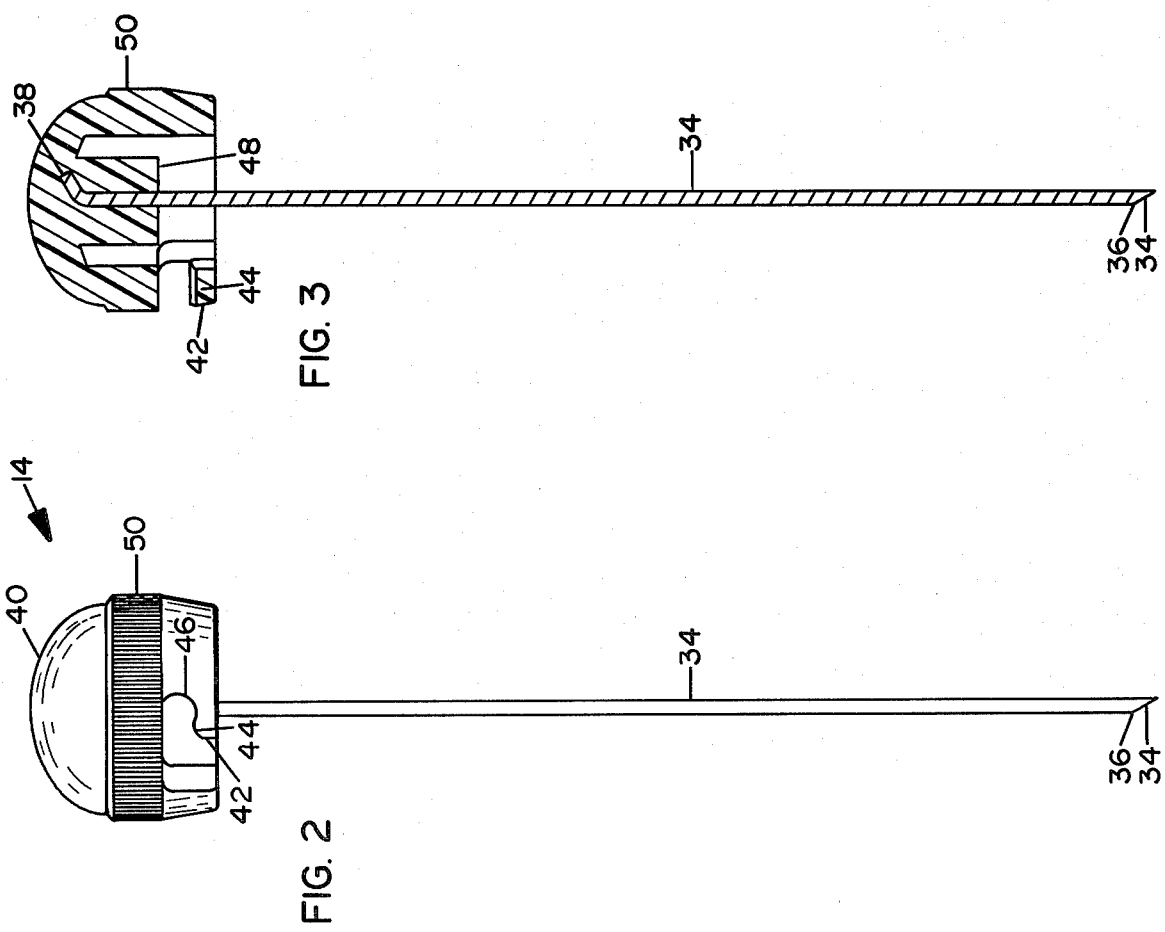

BONE MARROW ASPIRATION NEEDLE

CROSS REFERENCES TO CO-PENDING APPLICATIONS

This application is related to Biopsy Needle, Ser. No. 354,421, filed Mar. 3, 1982, assigned to the same assignee, and Biopsy Needle, Ser. No. 468,147, filed Feb. 22, 1983, at continuation of Ser. No. 244,015, filed Mar. 16, 1981.

BACKGROUND OF THE INVENTION

1. Field of the Invention

The present invention pertains to a surgical instrument and, more particularly, pertains to a biopsy needle which can either be disposable or reusable.

2. Description of Prior Art

The prior art biopsy needles have all presented some type of drawbacks when used by the physician or surgeon, and which are particularly less than desirable. Some prior art instruments are disposable and cast with very few structural details attended to, with the result that the interlocking between the stylet and the cannula provides for considerable play and the instrument can come apart in the user's hands, resulting in injury not only to the patient but more so to the user by the sharp metal edges poking upwards into the physician's hands. Other prior art devices have some form of interlocking structure but the interlocking structure is not positive, resulting in play between the cannula and stylet during the process of incision into the patient resulting in considerable discomfort. Other types of prior art structures have numerous components which during surgery are not practical in utilization by the user due to the screwing and unscrewing of the fittings.

More importantly, all of the prior art devices have grips which do not really fit into the physician's hand to provide for positive gripping by the physician but have grips which are required to be engaged by the physician in a negative way making the process of biopsy as uncomfortable to the physician/surgeon using the sternum needle as to the patient. The prior art has failed to recognize that the handles of a biopsy needle must securely engage into the physician's or surgeon's palm for optimum control of the instrument during a biopsy. It is also necessary that the sytlet and cannula be engaged to each other during the biopsy process for providing total control to the physician or surgeon.

The present invention overcomes the disadvantages of prior art references by providing a biopsy needle having a winged handle, detent locking between the stylet and cannula, and an adjustable threaded depth stop.

SUMMARY OF THE INVENTION

The general purpose of the present invention is to provide a biopsy needle having a cannula and a stylet, both of which engage and interlock with respect to each other, and which can be conveniently grasped by the physician or surgeon in the palm of the hand to provide secure control during the biopsy process with an adjustable depth stop on a threaded portion of the cannula.

According to one embodiment of the present invention, there is provided a biopsy needle having a cannula member and a stylet member which interlock with respect to each other, the cannula member including a cannula clip of a partial cylinder having two opposing formed members extending perpendicularly outward on an upper portion of the cannula, the end having a hollow-ground, beveled angle providing a knife-sharp edge in the range of 20°–30°, a molded housing formed thereabout of said cannula and about a portion of the clip, two vertical hand wings extending from an upper portion and a threaded lower portion, a button extending outwardly from an upward vertical member of reduced diameter with respect to the housing, and an internal bore of decreasing diameter extending through the housing to the top of the cannula for accepting a syringe for drawing of bone marrow during the biopsy, a stylet including one angled end for securing into a stylet cap and an other end having a hollow-ground beveled end in the range of 20°–30° and buffed to a polish having a knife-sharp edge about the tip, the stylet cap secured about the angled end of the stylet and having a spring detent locking groove for engaging under and about the button of the cannula in a detent-locking fashion, and an interior bore of a height to mate with the vertical member of the cannula and engage on the rim of the cannula formed between the housing and the vertical member and a threaded depth stop including a knurled circumference and a plurality of digitory sockets, a threaded interior bore to engage with the threaded lower portion of the molded housing whereby the stylet is engaged into the cannula housing and detent locks between the button on the cannula housing and the detent locking groove in the stylet cap providing for proper engagement between the knife-sharp edges of the cannula and the stylet and the depth stop is adjustable on the cannula about the threads, thereby providing for proper instrumentation during biopsy.

A significant aspect and feature of the present invention is a biopsy needle having wing-shaped handles facilitating gripping and engagement by the physician/surgeon user.

Another significant aspect and feature of the present invention is an interlocking stylet and cannula providing for not only interlocking of the structural members in a positive detent fashion but also predetermined orientation between the knife-sharp edges of the cannula and the stylet. The inter-locking structure also positions the stylet at a proper distance from the cannula, providing for consistent and secure biopsy surgery.

A further significant aspect and feature of the present invention is a biopsy needle which can be constructed either as a disposable instrument or as a reusable instrument depending upon the type of molded material chosen for the cannula and stylet housings.

An additional significant aspect and feature of the present invention is a biopsy needle which can be constructed in different sizes for different sized individuals or for different applications.

Having described one embodiment of the present invention, it is the principal object hereof to provide a sternum or iliac needle including a cannula and stylet which interlock with each other and a threaded adjustable depth stop. The disclosure also applies to needle structure per se, and is not to be construed as being limited only to biopsy needles, as other applications are inherent within the scope of this disclosure.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates an engaged front view of a sternum or iliac needle, the present invention, including a stylet, adjustable depth stop, and a cannula;

FIG. 2 illustrates a front view of the stylet;

FIG. 3 illustrates a sectional view of the stylet;

FIG. 4 illustrates a sectional view of the cannula;

FIG. 5 illustrates a sectional view of the cannula, depth stop and stylet all engaged with respect to each other;

FIG. 6 illustrates a sectional view taken along line 6—6 of FIG. 5; and,

FIG. 7 illustrates a sectional view taken on line 7—7 of FIG. 5.

DESCRIPTION OF PREFERRED EMBODIMENTS

FIG. 1 illustrates a front view of a sternum or iliac needle 10 having engageable components of a cannula member 12, a stylet member 14, and a depth stop 16. The cannula member 12 includes a longitudinal cannula 17 having a knife-sharp edge 18 which has been ground, buffed and polished outwardly at an angular tubular relationship and a molded housing 20 of acrylonitrile butadiene styrene (ABS) material or the like having the shape as illustrated in the figure. The housing 20 includes molded thereto left-hand wing 22 and right-hand wing 24, a vertical member 26 extending upwardly, an elongated button 28 extending outwardly in FIG. 4, an angled chamber 30 running vertically downward from the top of member 26 and a threaded lower portion 32. The stylet member 14 includes a metal stylet 34 having a sharp edge 36 which has been ground, buffed and polished, a bent end 38 of FIG. 3 for securing into a rounded molded cap 40, a detent locking groove 42 having an inherent spring member 44 including positive locking member 46. A downward extending boss 48 of FIG. 3 extends downwardly internal to the cap 40 for engagement with a rim 28a of the cannula housing 20. A knurled circumference 50 is provided about the cap for engagement by physician/surgeon user. The edges 18 and 36 are hollow ground flush with each other, with a hollow beveled angle in the range of 15°–40°, preferably 25°.

The depth stop 16 includes an upper knurled outer circumference 68, a threaded inner portion 70 as illustrated in FIG. 5, an outer flared lower portion 72 between the upper knurled portion 68 and a rounded edge 74, and a plurality of digitory sockets 76a–76d spaced about the edge 74 as also illustrated in FIG. 7.

FIG. 2 illustrates a front view of the stylet 14 where all numerals correspond to those elements previously described. Attention is drawn to the lock groove 42 and the knife edge 36.

FIG. 3 illustrates a sectional view of the stylet member 14 where all numerals correspond to those elements previously described. The end of the stylet has an angle of 25° to the vertical while the angle may be in the range of 20°–30°. The tip is ground, buffed, and polished to maintain a knife-sharp edge. The upper end 38 of the stylet 34 is angled for securing into the rounded cap 40 during molding.

FIG. 4, which illustrates a sectional view of the cannula member 12, shows the particular detail of a cannula clip 50 securing the cannula 17 into the housing 20 about the angled chamber 30. The angled chamber 30 decreases from a large diameter 52 to a small diameter 54 in a luer taper, then to a chamfer 56, of a diameter which is slightly greater than the internal diameter of the cannula 16 so that a syringe can be inserted into the angled chamber 30 to draw bone marrow up into the cannula. A probe can be utilized to freely push the bone marrow out through the beveled end of the cannula and onto a slide, without damaging or distorting the bone marrow. The detent button 28 and the rim 28a provide for engagement of the stylet member 14 in proper predetermined orientation. The cannula clip 50 is silver soldered to the cannula 17 at an upper mid portion and is molded into the housing 20. The clip as also illustrated in FIG. 6 includes a partial circular portion 58 and two wings 60 and 62 extending outwardly therefrom. A lower portion 64 of the housing 20 includes a plurality of threads 66.

FIG. 5 illustrates a sectional enlarged view of elements engaged with respect to each other for use as a biopsy needle in a medical biopsy procedure. All numerals correspond to those elements previously described. Particular distinction is drawn to the movability of the depth stop 16 with respect to the housing 20 in relation of the threads 70 of the depth stop 16 to the threads 66 of the cannula member 12. The cannula clip is a silver soldered to cannula 17 of the cannula member thereby securing it in place. The cannula 17 with the cannula clip 50 and the wings is molded into the housing 20, thereby securing the cannula 17 with respect to the housing 20. The threads 66 are likewise molded into the lower portion of the cannula housing.

FIG. 6, which illustrates a sectional view taken along line 6—6 of FIG. 5, shows the cannula clip with respect to the cannula 17 and the cannula housing 20. The particular angle between the ears 60 and 62 is preferably in the range of 60°–120° and in this instance 90°.

FIG. 7 illustrates a sectional view taken on line 7—7 of FIG. 5 and shows particularly the digitory sockets 76a–76d spaced about the edge 74 of the depth stop 16. The knurled circumference 68 is also illustrated accordingly as well as that of the knurled skirt 74 which provide for grasp while the digitory sockets provide for transfer of digitory pressure.

MODE OF OPERATION

FIG. 1 best illustrates the biopsy needle 10 for biopsies, the present invention, where the stylet 14 is engaged and interlocked with respect to the cannula member 12. The depth stop 16 is appropriately screwed and adjusted to a point as determined by the physician/surgeon depending upon the depth of penetration of the needle for the particular physical size of the individual and the particular placement of the needle in the body with respect to fatty tissue and the marrow in the bone.

The detent button 28 provides for interlocking and interengagement of the members 12 and 14 together through engagement of the groove 42, up and over the spring member 44, and into the positive locking detent 46. The spring member 44 provides a positive sensory digital feedback signal indicating that the members 12 and 14 are engaged when button 28 resides within the chamber area of the positive locking chamber 46. The button 28 and the positive locking chamber 46 always indicate that the hollow-ground beveled angle of 25° of each of the knife edges 18 and 36 of the members are always oriented with respect to each other, as illustrated in FIGS. 1 and 5.

The depth stop 16 seats the sternum needle onto the individual's skin at the proper predetermined distance and provides for proper penetration of the knife edges. The knife-sharp edges arranged at the hollow beveled angle and flush to each other provides for the proper cutting action through the skin, tissue and bone due to the wedge action of the tips. The particular angles of the wedges and orientation with respect to each other is one of the important factors in obtaining a suitable bone marrow sample from the sternum during the biopsy process, as well as determining the proper distance without exceeding or being short in obtaining the sample. The threaded engagement of the depth stop 16 about the threaded member 64 to the lower portion of the cannula housing 20 provides for predetermining that particular distance and the digital sockets 76a–76d provide for adjustment by the physician/surgeon during the biopsy as well as the knurled portion 68.

The contour of the handles 22 and 24 provides a wing configuration feedback positive feel to the physician/surgeon during the biopsy as well as the digitory pads 76a–76d as adjustment is required. The knurled portions 68 and 50 of the depth stop 16 and the rounded stylet handle 14 provide the final digital grasping members of the needle 10 along with the knurled skirt 74 along with the sockets 76a–76d. The fingers of the physician/surgeon can apply pressure through the sockets as well as the rounded head, and can grasp any of the knurled portions for a secure grasp during biopsy.

The depth stop is 16 can be carefully adjusted during a sternum biopsy so that the needle does not protrude through the sternum, especially through the other side of the sternum and through the arota. Depending upon the size of the individual, the depth stop 16 may be removed from the cannula member-stylet member to reach the iliac, and hence, would not be used. The considerations are made by the physican/surgeon at the time of the biopsy, and are also dependent upon the individual's own size.

Various modifications can be made to the present invention without departing from the apparent scope thereof. The wings or ears of the cannula member can take any desired shape as well as any angle between the wings or ears. The clip can also be positioned anywhere within the mold body of the cannula housing 20 so as to be molded therein.

Having thus described the invention, what is claimed is:

1. Needle comprising:
    a. cannula member, said cannula member including a tubular cannula, a cannula clip fixedly secured on an upper portion of said tubular cannula and having two opposing ears extending substantially angularly outward therefrom, a lower end of said tubular cannula including a hollow-ground beveled knife-sharp edge angle, a molded housing formed thereabout of said tubular cannula wherein said opposing ears are permanently embedded in said molded housing to prevent said cannula member from rotation with respect to said molded housing, two hand wings extending from an upper portion of said molded housing, said molded housing including a threaded lower portion, a button extending outwardly from an upwardly extending vertical member including a rim, the vertical member being of reduced diameter with respect to said molded housing and extending therefrom, and an angled chamber of reduced diameter extending through said vertical member to a top of said tubular cannula;
    b. stylet member including a stylet having an upper angled end for securing and an other end including a hollow-ground beveled knife-sharp angle, a stylet cap molded about said angled end of said stylet, and including a spring detent locking groove for engaging under and about said button of said cannula in a detent locking mode, an interior bore of a height to engage about and with said vertical member of said cannula and engaging on said rim of said cannula member; and
    c. threaded depth stop means including a knurled circumference and plurality of digitory sockets formed about an upper edge of said knurled circumference, and a threaded inner portion for adjustment over said lower threaded portion of said cannula member whereby said stylet of said stylet member is pushed through said tubular cannula and protruding beyond the end of the tubular cannula where the end of said tubular cannula and the stylet are in predetermined oriented relationship when said detent locking groove spring on twisting engages and locks with said button of said cannula and said detent locking groove of said stylet cap providing said respective orientation of said knife-sharp edges, said depth stop is adjustable on said threaded lower portion of said cannula providing for proper penetration of said cannula and said stylet during biopsy whereupon the stylet is removed and a syringe is inserted therein for the drawing of bone marrow up through said tubular cannula to said syringe.

2. Needle of claim 1 wherein said tubular cannula edge is 25° plus or minus 5° with respect to the vertical axis of said tubular cannula.

3. needle of claim 1 wherein said cannula clip is soldered to said tubular cannula.

4. needle of claim 1 wherein said two ears are at an angle in the range of 60°–120° with respect to each other.

5. Needle of claim 1 wherein said molded housing and molded stylet cap is of acrylonitrile butadiene stryene material.

* * * * *